US011806022B2

(12) United States Patent
Okudan et al.

(10) Patent No.: US 11,806,022 B2
(45) Date of Patent: Nov. 7, 2023

(54) AUTOMATICALLY ADJUSTED MEDICAL SAW SYSTEM

(71) Applicants: ISTANBUL TEKNIK UNIVERSITESI, Istanbul (TR); ISTANBUL UNIVERSITESI—CERRAHPASA REKTORLUGU, Istanbul (TR)

(72) Inventors: Mustafa Okudan, Istanbul (TR); Faruk Asicioglu, Istanbul (TR); Ali Gelir, Istanbul (TR)

(73) Assignees: ISTANBUL TEKNIK UNIVERSITESI, Istanbul (TR); ISTANBUL UNIVERSITESI—CERRAHPASA REKTORLUGU, Istanbul (TR)

( * ) Notice: Subject to any disclaimer, the term of this patent is extended or adjusted under 35 U.S.C. 154(b) by 151 days.

(21) Appl. No.: 17/607,903

(22) PCT Filed: Sep. 18, 2020

(86) PCT No.: PCT/TR2020/050865
§ 371 (c)(1),
(2) Date: Nov. 1, 2021

(87) PCT Pub. No.: WO2021/054925
PCT Pub. Date: Mar. 25, 2021

(65) Prior Publication Data
US 2022/0175396 A1 Jun. 9, 2022

(51) Int. Cl.
*A61B 17/14* (2006.01)
*A61B 90/11* (2016.01)
(Continued)

(52) U.S. Cl.
CPC ............ *A61B 17/147* (2016.11); *A61B 90/11* (2016.02); *A61B 90/14* (2016.02);
(Continued)

(58) Field of Classification Search
CPC . A61B 17/147; A61B 90/11; A61B 2090/061; A61B 2090/062; A61B 2090/08021; A61B 17/14
See application file for complete search history.

(56) References Cited

U.S. PATENT DOCUMENTS 10,194,922 B2 * 2/2019 Bono .................. A61B 17/1624
11,432,828 B1 * 9/2022 Lang .................... A61B 17/142
(Continued)

FOREIGN PATENT DOCUMENTS

| AU | 2019201451 A1 | 3/2019 |
| AU | 2017372911 A1 | 6/2019 |

(Continued)

*Primary Examiner* — Julian W Woo
(74) *Attorney, Agent, or Firm* — Bayramoglu Law Offices LLC

(57) ABSTRACT

An automatically adjusted medical saw system has a mechanism that measures bone thickness via ultrasound-based sensors to ensure that only the bone tissue is cut during the cutting process and the soft tissue is not damaged during this cutting process. The automatically adjusted medical saw system includes a saw box, a saw blade, a movable platform, a saw motor, an ultrasonic receiver or a transmitter, a screw, a step motor, a hydrogel strip, a movement axis rail, a tightening apparatus, a motor control circuit, a control circuit for the ultrasonic receiver or the transmitter, a central control unit, and rails to guide the movable platform.

2 Claims, 3 Drawing Sheets

(51) Int. Cl.
*A61B 90/14* (2016.01)
*A61B 90/00* (2016.01)
(52) U.S. Cl.
CPC ... *A61B 2090/061* (2016.02); *A61B 2090/062* (2016.02); *A61B 2090/08021* (2016.02)

(56) References Cited

U.S. PATENT DOCUMENTS

2005/0116673 A1    6/2005  Carl et al.
2007/0032620 A1*   2/2007  Gleason ................. C09D 4/00
                                                     526/217

FOREIGN PATENT DOCUMENTS

| | | |
|---|---|---|
| CN | 104490450 A | 4/2015 |
| CN | 106377293 A | 2/2017 |
| CN | 107397571 A | 11/2017 |
| CN | 207693632 U | 8/2018 |
| EP | 1974679 A2 | 10/2008 |
| WO | 2019057033 A1 | 3/2019 |

* cited by examiner

AUTOMATICALLY ADJUSTED MEDICAL SAW SYSTEM

CROSS REFERENCE TO THE RELATED APPLICATIONS

This application is the national phase entry of International Application No. PCT/TR2020/050865, filed on Sep. 18, 2020, which is based upon and claims priority to Turkish Patent Application No. 2019/14321, filed on Sep. 20, 2019, the entire contents of which are incorporated herein by reference.

TECHNICAL FIELD

The invention is related to an automatically adjusted medical saw system having a mechanism that measures bone thickness via ultrasound-based sensors that ensures that only the bone tissue is cut during the cutting process, that does not damage soft tissue during this cutting process and that prevents the scattering of bone and tissue pieces during the cutting process by a hydrogel-based covering material.

BACKGROUND

The basic principle of forensic autopsies is that the three areas of the body are opened, which are the head, chest and abdominal area. Therefore, in all of the autopsy cases, the skull needs to be opened. To this aim, in the world, commonly oscillating medical saws are used. Generally, the cutting tip of these saws is open. Additionally, in present systems the bone thickness cannot be measured during the bone cutting process.

Various developments have been carried out in the art, in relation to automatically adjusted medical saws.

In the American patent document numbered US2005116673A1 of the prior art, a system that is used to control the saw is disclosed. In this system, a sensor is used to control at least one process parameter of the device, such as drilling speed or acceleration. A data processing unit is used for instrumentation, and to determine characteristic values of the parameter such as, amplitude and frequency, and to process data that represents the parameter. These characteristic values are used to control the operation of the device, to determine one or more characteristics of the material applied by the device or to track the status of the device. Although the aspects of the invention can be applied to several assemblies, it is generally used to drill a hole into a bone or to cut a bone.

In the Australian patent document numbered. AU2019201451A1 of the prior art, a detection method to determine the depth (the depth of the oscillating saw blade) of penetration of the surgical tool used during the bone cutting process is disclosed.

In the Australian patent document numbered AU2017372911A1 of the prior art, a saw whose torque can be adjusted by the aid of a sensor is disclosed. The torque in the robot lever can be measured and adjusted by using a sensor.

The Chinese patent document numbered CN104490450A of the prior art belongs to the technical field of surgical procedures and it particularly mentions an electric saw with automatic cutter for an orthopaedic procedure. The automatic electric saw is characterized in that it comprises a bone saw body, moveable blocks, a sliding frame and brackets.

In the Chinese patent document numbered CN107397571A of the prior art, a pendulum saw and a method for controlling said saw is disclosed. The medical pendulum saw, comprises a motor, a speed sensor, a data processing unit and a back end server.

However, several problems are encountered during the procedures carried out with medical saws of the prior art. For example, even if the forensic experts are very cautious, the cerebral cortex and the brain tissue lying beneath the skull bone mostly are damaged during the cutting process of the skull. The distinction between an artefact or a traumatic cause of such an incision in the brain membrane and tissue often arises as a problem. Besides the medical saws that are being used currently being time and labour consuming, they may cause serious health problems to users of said saws. The dust particles, such as bone dust and very small sized tissue particles that are scattered during the process enter directly from the air or are suspended in the air and they enter through the orifices (from the eyes, mouth or nostrils even though protective gear such as masks, glasses etc are used) of the specialists that are using the saw and they may lead to various infections, and foreign matter reaction by entering the respiratory tract. The automatically adjusted medical saw system subject to the invention has been developed in order to solve the above mentioned problems.

SUMMARY

The aim of the invention is to provide an automatically adjusted medical saw system that comprises a mechanism that measures the skull bone thickness via ultrasound-based sensors, and ensures that only the bone tissue is cut during the cutting process and that does not damage the soft tissue that lies right beneath the bone tissue.

Another aim of the invention is to provide an automatically adjusted medical saw system that prevents bone powder and tissue particles from scattering or from being suspended in air by means of the usage of a hydrogel strip and by means of having its cutting tip inside a closed housing.

BRIEF DESCRIPTION OF THE DRAWINGS

The automatically adjusted medical saw system provided to reach the aims of the invention has been illustrated in the attached figures.

Figure 1:
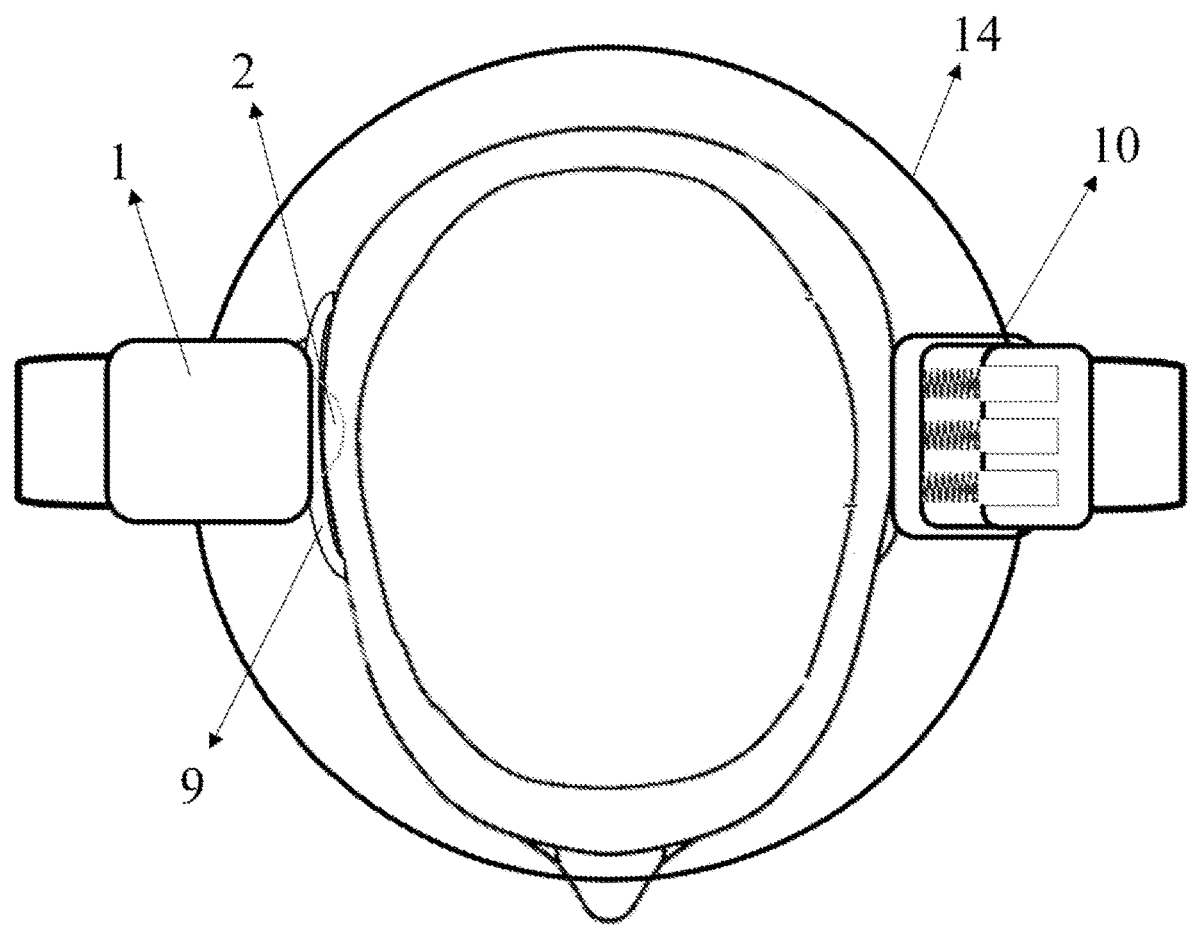
FIG. 1: Schematic top view of the automatically adjusted medical saw system comprising a saw box, support apparatus and hydrogel strip.
Figure 2:
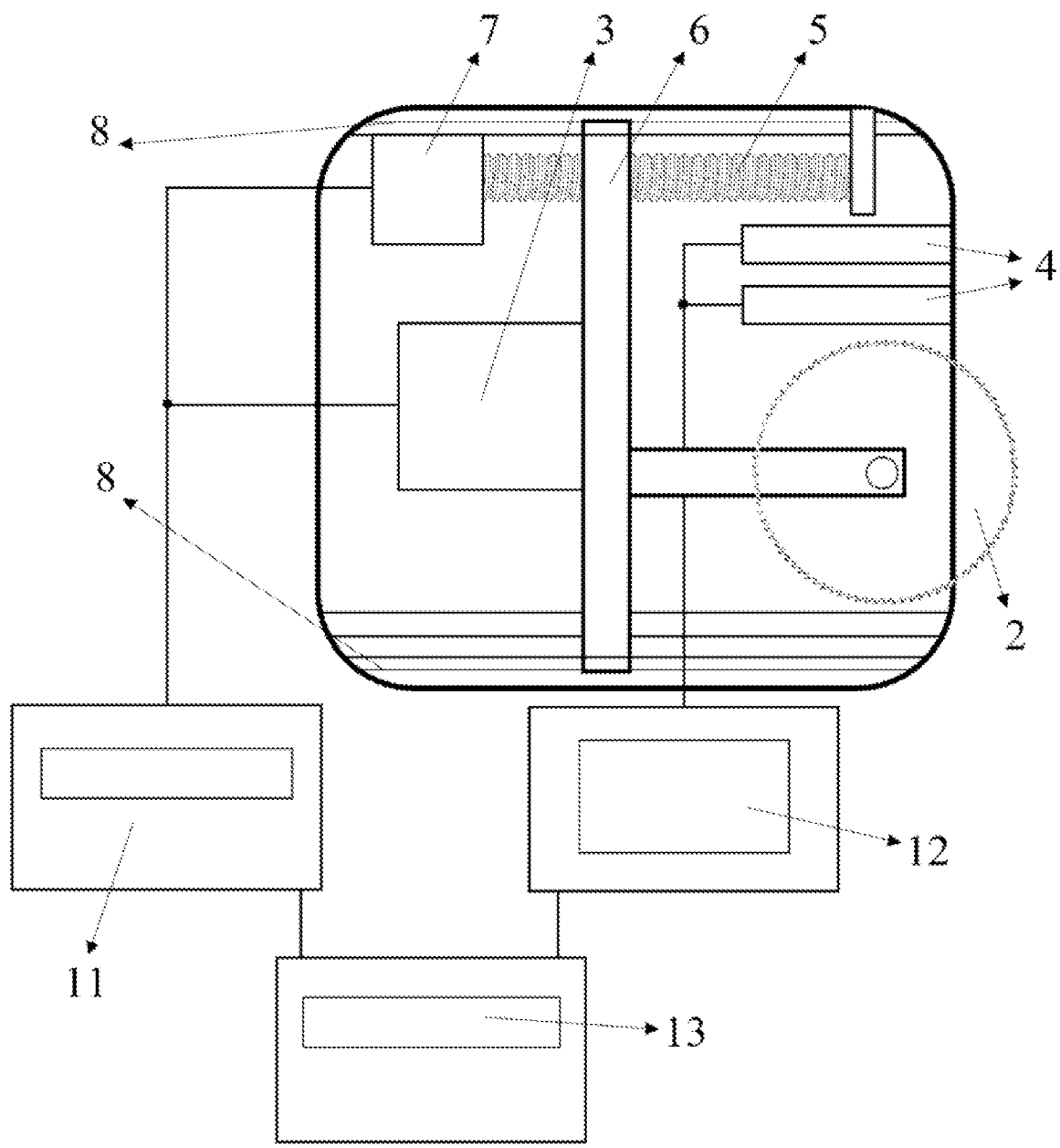
FIG. 2: Schematic view showing the inside of the saw box and the control units of the automatically adjusted medical saw system.
Figure 3:
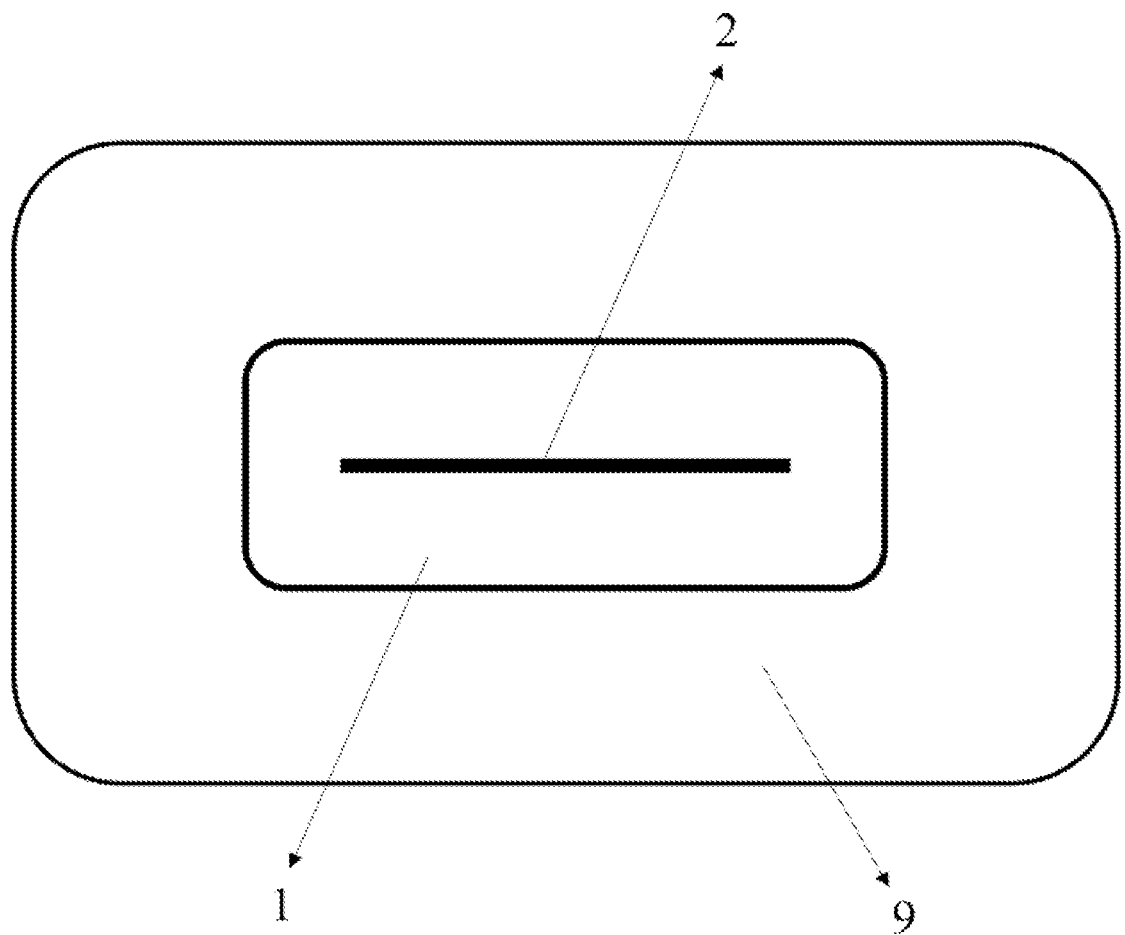
FIG. 3: Schematic bottom view of the saw box and hydrogel strip.

The parts in the figures have each been numbered and their references have been listed below.
1. Saw box
2. Saw blade
3. Saw motor
4. Ultrasound receiver/transmitter
5. Screw
6. Movable platform
7. Step motor
8. Rail
   Hydrogel strip
10. Tightening apparatus
11. Motor control circuit
12. Ultrasound receiver/transmitter control circuit
13. Central control unit
14. Movement axis rail

DETAILED DESCRIPTION OF THE EMBODIMENTS

The automatically adjusted medical saw system subject to the invention comprises;
- a saw box (1) that enables the cutting tip of the saw to remain in a closed area cutting tip of the saw is being operated,
- a saw blade (2) that is positioned inside the saw box (1), where a part of said saw blade is located outside the saw box (1),
- a movable platform (6) that is connected to the saw blade (2), and that is located at the rear section of the saw blade (2) that remains partially inside the saw box (1),
- a saw motor (3) that is connected to the saw blade (2) and that actuates the rotational motion of the saw blade (2),
- an ultrasonic receiver/transmitter (4) located in the saw box (1), that faces the section that is carrying out the cutting process,
- a screw (5) that extends longitudinally inside the saw box (1), which is connected to one end of the movable platform (6),
- a step motor (7) positioned at the end of the screw (5) that provides the rotational motion to the screw (5),
- a rail (8) that is positioned at the top and bottom section of the saw box (1), which guides the movable platform (6),
- a hydrogel strip (9) that is located on the cutting surface of the saw box (1), which envelopes the saw blade (2),
- a movement axis rail (14) that moves on the saw box (1) and that envelopes the tissue to be cut,
- a press apparatus (10) located on the movement axis rail (4) that continuously clamps the saw box to ensure full contact to the skull surface,
- a motor control circuit (11) that is connected with the saw motor (3) and the step motor (7),
- an ultrasonic receiver/transmitter control circuit (12) connected with the ultrasonic receiver/transmitter (4),
- a central control unit (13) connected to the motor control circuit (11) and ultrasonic receiver/transmitter circuit (12).

The bone thickness is instantaneously measured by means of the ultrasonic receiver/transmitters (4) and the cutting depth of the saw is automatically adjusted according to the thickness value received from the ultrasonic receiver/transmitter (4). This adjustment process is carried out by the step motor (7) which enables to slide the movable platform (6) on rails (8). The movement of the saw blade (2) is adjusted following the sliding of the movable platform (6) on the rails (8). The system comprises a motor control circuit (11) and an ultrasonic receiver transmitter control unit (12) that are connected ultrasonic receiver/transmitter (4) and the step motor (7). The controlling of all of these parts is performed by the central control unit (13).

The saw operates inside a closed housing, or in other words inside the saw box (1). Bone powder and tissue residue is prevented from being scattered, by means of the hydrogel strip (9) that is located on the cutting surface of the saw box (1), which envelopes the saw blade (2). The reason for this is that this bone dust and tissue residues, are captured by the hydrogel strip (9). While the saw continues its cutting process, the continuous contact of the saw blade (2) with the tissue is provided by means of the tightening apparatus (10). The tightening apparatus (10) is a mechanism that includes a spring therein, whose height automatically increases or decreases while the system is rotating around the skull. The cutting process starts at the point where the skull diameter is at a maximum and when the areas where the diameter is reduced is reached, the compresses springs that are located inside the tightening apparatus are opened and it is enabled for the saw to continuously be in contact with the skull. As a result, the cutting process is performed at the depth values that are desired and therefore, the problems that may arise are minimized.

What is claimed is:

1. An automatically adjusted medical saw system, comprising:
   - a saw box, wherein the saw box enables a cutting tip of a saw to remain in a closed area when the cutting tip of the saw is being operated,
   - a saw blade, wherein the saw blade is positioned inside the saw box, and a part of the saw blade is located outside the saw box,
   - a movable platform, wherein the movable platform is connected to the saw blade, and the movable platform is located at a rear section of the saw blade partially inside the saw box,
   - a saw motor, wherein the saw motor is connected to the saw blade, and the saw motor actuates a rotational motion of the saw blade,
   - an ultrasonic receiver or a transmitter, wherein the ultrasonic receiver or the transmitter is located in the saw box, and the ultrasonic receiver or the transmitter faces a section of the saw box carrying out a cutting process, and the ultrasonic receiver or the transmitter is configured to instantaneously measure a bone thickness,
   - a screw, wherein the screw extends longitudinally inside the saw box, and the screw is connected to one end of the movable platform,
   - a step motor, wherein the step motor is positioned at one end of the screw and provides a rotational motion to the screw,
   - a hydrogel strip for capturing bone dust and/or tissue residues, wherein the hydrogel strip is located on a surface of the saw box, and the hydrogel strip envelopes the saw blade,
   - a movement axis rail, wherein the movement axis rail moves on the saw box, and the movement axis rail is configured to surround an area where the saw will operate,
   - a tightening apparatus, wherein the tightening apparatus is located on the movement axis rail and continuously clamps the saw box to ensure a full contact to a surface of an object to be cut,
   - a motor control circuit, wherein the motor control circuit is connected with the saw motor and the step motor,
   - a control circuit for the ultrasonic receiver or the transmitter, wherein the control circuit is connected with the ultrasonic receiver or the transmitter,
   - a central control unit, wherein the central control unit is connected to the motor control circuit and the control circuit for the ultrasonic receiver or the transmitter,
   - wherein a cutting depth of the saw is automatically adjusted according to the bone thickness received from the ultrasonic receiver or the transmitter.

2. The automatically adjusted medical saw system according to claim 1, further comprising a first rail positioned at a top section of the saw box and a second rail positioned at a bottom section of the saw box to guide the movable platform.

* * * * *